United States Patent
Poorter (10) Patent No.: US 8,284,894 B2
(45) Date of Patent: Oct. 9, 2012

(54) FAST TOMOSYNTHESIS SCANNER APPARATUS AND CT-BASED METHOD BASED ON ROTATIONAL STEP-AND-SHOOT IMAGE ACQUISTION WITHOUT FOCAL SPOT MOTION DURING CONTINUOUS TUBE MOVEMENT FOR USE IN CONE-BEAM VOLUME CT MAMMOGRAPHY IMAGING

(75) Inventor: Tiemen Poorter, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 191 days.

(21) Appl. No.: 12/933,922

(22) PCT Filed: Mar. 26, 2009

(86) PCT No.: PCT/IB2009/051257
§ 371 (c)(1), (2), (4) Date: Sep. 22, 2010

(87) PCT Pub. No.: WO2009/122328
PCT Pub. Date: Oct. 8, 2009

(65) Prior Publication Data
US 2011/0026667 A1 Feb. 3, 2011

(30) Foreign Application Priority Data
Mar. 31, 2008 (EP) ................................ 08103234

(51) Int. Cl.
*G01N 23/00* (2006.01)

(52) U.S. Cl. .......................................... 378/22; 378/21

(58) Field of Classification Search .............. 378/21–27, 378/12
See application file for complete search history.

(56) References Cited

U.S. PATENT DOCUMENTS

| | | | |
|---|---|---|---|
| 5,313,510 A | 5/1994 | Ebersberger et al. | |
| 5,544,216 A | 8/1996 | Norhager | |
| 6,960,020 B2 * | 11/2005 | Lai | 378/207 |
| 7,110,490 B2 | 9/2006 | Eberhard et al. | |
| 7,212,606 B2 * | 5/2007 | Souchay et al. | 378/37 |
| 2004/0066884 A1 | 4/2004 | Claus et al. | |
| 2004/0109529 A1 * | 6/2004 | Eberhard et al. | 378/23 |
| 2005/0105679 A1 | 5/2005 | Wu et al. | |

FOREIGN PATENT DOCUMENTS

WO 2008037731 A2 4/2008

OTHER PUBLICATIONS

Kachelriess et al.: Flying Focal Spot (FFS) in Cone-Bean CT; Nuclear Science Symposium Conference, IEEE, 2004, pp. 3759-3763.

* cited by examiner

Primary Examiner — Hoon Song (57) ABSTRACT

The present invention generally refers to computed tomography (CT) based imaging systems and, more particularly, to a fast 3D tomosynthesis scanner apparatus and CT-based method without focal spot motion during continuous tube movement around an object of interest (O) or tissue region (M) to be examined (herein also referred to as "object"), which may advantageously be used in cone-beam volume CT mammography imaging so as to avoid motion artifacts and blurring effects.

15 Claims, 5 Drawing Sheets

FAST TOMOSYNTHESIS SCANNER APPARATUS AND CT-BASED METHOD BASED ON ROTATIONAL STEP-AND-SHOOT IMAGE ACQUISTION WITHOUT FOCAL SPOT MOTION DURING CONTINUOUS TUBE MOVEMENT FOR USE IN CONE-BEAM VOLUME CT MAMMOGRAPHY IMAGING

FIELD OF THE INVENTION

The present invention generally refers to computed tomography (CT) based imaging systems and, more particularly, to a fast 3D tomosynthesis scanner apparatus and CT-based method for rotational step-and-shoot image acquisition without focal spot motion during continuous tube movement around a breast tissue to be examined, which may advantageously be used in cone-beam volume CT mammography imaging so as to avoid motion artifacts and blurring effects.

BACKGROUND OF THE INVENTION

CT and MRI mammography are currently the most effective breast cancer screening techniques. Conventional mammography techniques rely on a pair of 2D X-ray images of the female breast, taken from two different directions: from the top to the bottom and from one side to the other. The breast tissue to be examined is compressed and held between two glass plates to ensure that the whole breast tissue is viewed. Nowadays, full-field digital mammography (FFDM) systems are commonly used which are e.g. based on real-time amorphous silicon ($\alpha$-Si) or amorphous selenium ($\alpha$-Se) flat panel detector (FPD) technology.

Although it has been shown in numerous clinical studies that mammography helps to achieve a reduction of breast cancer mortality rate by 30% to 50%, mammography is not a perfect imaging technique, which is due to the fact that about 30% of breast cancers are typically missed. Interpreting a mammogram is difficult due to superimpositions of the breast tissue, which makes small cancerous tissue regions and other pathological tissue anomalies sometimes undetectable. In clinical breast imaging, tumors and other tissue anomalies can be obscured by normal breast-tissue elements lying outside a plane of interest, thus leading to false-negative results and decreasing sensitivity. Conversely, superimposed tissue elements are known to give the appearance of a tissue abnormality and may lead to false-positive lesions that appear like a cancerous tumor on a mammogram, which is one reason for unnecessary call-backs of the patient in conventional 2D mammography.

In contrast to conventional 2D mammography, digital breast tomosynthesis (DBT) is an exciting new development in breast imaging which yields multiple high-resolution image slices located at different depth in a breast volume. DBT thereby provides three-dimensional structural information of the female breast by reconstructing (e.g. based on a standard inverse 3D Radon transform in conjunction with the filtered backprojection algorithm) a volumetric view from a series of e.g. eleven low-dose two-dimensional projection images of a compressed breast acquired at multiple projection angles during a sweep of the X-ray tube over a circular arc segment of e.g. 50°. Objects at different heights in the breast are projected differently at different angles. The subsequent image reconstruction leads to a stack of slice images of the different depth layers parallel to the detector surface. The in-slice resolution is predominantly determined by the detector resolution and usually much higher than the resolution between different slices ("depth resolution") due to the incomplete sampling of the object within a relatively small angular scan range. This technique enables physicians to "page through" the interior of the female breast without obstruction by surrounding superimposed tissue.

As a result, DBT greatly reduces the problems of superimposed tissue that may obscure tumors or create the illusion of cancer. Other researchers have investigated tomosynthesis for applications such as angiography, chest imaging, hand joint imaging and dental imaging. The diagnostic capability of DBT may be further improved by the use of contrast agent providing "functional" information of the breast lesion.

However, since DBT volumetric images are computed using a complex algorithm known as maximum-likelihood expectation maximization (MLEM), the DBT method involves vast amounts of computation, which previously took far too long for being applied in a clinical setting. Nonetheless, early results with DBT are promising. Researchers believe that this novel breast imaging technique will make breast cancers easier to see in dense breast tissue and will make breast screening more comfortable.

Not only have the researchers shown that they will be able to find more cancers earlier, but they will also be able to reduce many of the false alarms that occur when using conventional mammography due to the overlap of normal structures in the breast. DBT virtually eliminates these false-positive studies. This will save a great deal of anxiety for many women and will reduce the overall cost of breast cancer screening while improving its accuracy.

Results of earlier clinical studies indicate that diagnostic breast tomosynthesis improves the ability to analyze lesion margins and distinguish malignant from benign tumors. This improved diagnostic information results in better identifying a correct target for biopsy, helps analyze tumor margins and the extent of breast cancer while helping to reduce the overall number of biopsies performed.

SUMMARY OF THE INVENTION

In a conventional DBT system, the total time which is required for an image acquisitions is determined by the total integration time $T_{int}$ of all required images (the number N of images will probably be, for example, between about 11 and 55) and the total time $T_{move}$ required to move the X-ray tube between the image positions. To obtain the best possible quality of the acquired X-ray images, the image acquisition procedure should use a stop-and-shoot method where the X-ray tube is stationary during image integration time $T_{int}$. Image acquisition can then not take place during a movement of the X-ray tube (including the time of becoming mechanically stable—an unintended movement—after stopping the intended movement). However, when such a procedure is used, total acquisition time $T_{acq}=T_{int}+T_{move}$ is relatively long. Since the available acquisition time $T_{acq}$ should preferably be limited to less than e.g. ten seconds and preferably to less than e.g. eight seconds, total time $T_{int}$ that actually remains for the imaging becomes short. Some suppliers even seem to accept focal spot motion which occurs if the X-ray tube is moved during image acquisition. This, however, may lead to serious image blur which significantly reduces the obtained image quality.

It may thus be an object of the present invention to provide a tomosynthesis scanner apparatus and CT-based method with an enhanced image quality free of motion artifacts and blurring effects which may arise in conventional DBT systems due to the continuous rotational movement of the X-ray tube and its focal spot position along an arc segment of a circular trajectory around a breast tissue to be examined.

In view of this object, a first exemplary embodiment of the present invention is dedicated to a novel 3D tomosynthesis scanner apparatus adapted to perform a rotational step-and-shoot image acquisition procedure for acquiring a set of 2D projection images during a continuous rotational movement of a rotary X-ray tube in an azimuthal direction along an arc segment of a circular trajectory when rotating around an object of interest or a tissue region to be examined (in the following also referred to as "object") and subjecting these 2D projection images to a 3D reconstruction procedure. According to the present invention, it is foreseen that, during the image acquisition time for each 2D projection image, the electron beam focal spot on the rotary X-ray tube's anode is moved in an opposite direction along the same arc segment from a start position to an end position with respect to the rotary X-ray tube's housing such that the azimuthal path distance covered by the rotary X-ray tube due to the continuous rotational tube movement during this time is compensated. In this context, it should be noted that the compensation movement of the focal spot does not need to be accurate on a micrometer scale, which is because an accuracy with a tolerance of up to a few hundred micrometers would already result in a large improvement in a practical system.

The 3D tomosynthesis scanner may further comprise a mechanism for switching the electron beam focal spot back to its start position with respect to said tube housing before starting a new image acquisition process for acquiring the image data of a next 2D projection image of said object of interest or tissue region to be examined.

Said 3D tomosynthesis scanner apparatus may thus be adapted for performing a superposition of the electron beam focal spot's compensation movement to the X-ray tube's continuous rotational movement. Thereby, said compensation movement may be defined by a time-variant discontinuous sawtooth function describing said electron beam focal spot's momentary position on the arc segment of the circular trajectory along which said X-ray tube is moved over the time. It may advantageously be foreseen that said time-variant discontinuous sawtooth function is given by a stepwise linear function with an inverse slope factor as compared to the slope factor of a linear time-variant function describing the X-ray tube's momentary position over the time. The azimuthal path distance to be compensated is a linear function of the difference in azimuth covered by the electron beam focal spot (with the radial distance between the center of rotation and the focal spot position on the circular arc segment being a proportionality factor of this linear function) when being moved from said start position to said end position with respect to the rotary X-ray tube's housing. A superposition of the focal spot movement with respect to the tube housing and the continuous rotational movement of the rotary X-ray tube along the circular arc segment thereby results in a stationary focal spot position relative to the object and a stationary X-ray detector diametrically oppositely arranged to the X-ray tube with respect to said object.

According to a further aspect of the present invention, it may be foreseen that the proposed 3D tomosynthesis scanner apparatus comprises a first position sensor unit for detecting the momentary position of the electron beam focal spot on the rotary X-ray tube's anode with respect to said X-ray tube's housing. In addition to that, said 3D tomosynthesis scanner apparatus may comprise an actuator unit for moving the electron beam focal spot on the rotary X-ray tube's anode from said start position to said end position and an actuator control unit for controlling the actuator unit in a closed-loop control based on the momentary position of the electron beam focal spot continuously detected by said first position sensor unit and the rotary X-ray tube's momentary position on the arc segment of the of the circular trajectory, the latter momentary position being detected by a second position sensor unit. The actuator unit may thereby be equipped with a field generator device for generating an electric and/or magnetic field which is needed to deflect an electron beam impinging on the X-radiation emitting surface of said rotary X-ray tube's anode such that the resulting electron beam focal spot is moved along the circular trajectory from said start position to said end position.

A second exemplary embodiment of the present invention refers to an image acquisition, processing, visualization and archiving system which comprises a 3D tomosynthesis scanner apparatus according to anyone of the preceding claims.

A third exemplary embodiment of the present invention is directed to a method for operating a 3D tomosynthesis scanner apparatus comprising a rotary X-ray tube and a stationary X-ray detector diametrically oppositely arranged to the X-ray tube as described above with reference to said first exemplary embodiment. Said method thereby comprises the steps of performing a rotational step-and-shoot image acquisition procedure for acquiring a set of 2D projection images during a continuous rotational movement of the rotary X-ray tube in an azimuthal direction along an arc segment of a circular trajectory when rotating around an object of interest or a tissue region to be examined and subjecting these 2D projection images to a 3D reconstruction procedure. According to the present invention, it is foreseen that, during the image acquisition time for each 2D projection image, the electron beam focal spot on the rotary X-ray tube's anode is moved in an opposite direction along the same arc segment from a start position to an end position with respect to the rotary X-ray tube's housing such that the azimuthal path distance covered by the rotary X-ray tube due to the continuous rotational tube movement during this time is compensated. In this way, the X-ray focus (seen from an arbitrary point in a stationary inertial system) is stationary in space during the acquisition of each one from a series of individual 2D projection images showing said object from a variety of different projection angles during the continuous rotational movement of the rotary X-ray tube.

In addition to that, said method may comprise the step of switching the focal spot back to its start position with respect to said tube housing before starting a new image acquisition process for acquiring the image data of a next 2D projection image of said object of interest or tissue region to be examined.

The compensation of said azimuthal path distance may thus be achieved by a superposition of a compensation movement of said electron beam focal spot to the X-ray tube's continuous rotational movement, said compensation movement being defined by a time-variant discontinuous sawtooth function describing said focal spot's momentary position over the time. Said sawtooth function may preferably be given by a stepwise linear function with an inverse slope factor as compared to the slope factor of a linear time-variant function describing the X-ray tube's momentary position over the time.

The above-described method may further comprise the steps of continuously detecting the momentary position of the rotary X-ray tube during the continuous rotational movement around the object of interest or tissue region to be examined and controlling an actuator unit applied for moving the focal spot on the rotary X-ray tube's anode along the arc segment of said circular trajectory from said start position to said end position with respect to the rotary X-ray tube's housing dependent on the momentary position of the rotary X-ray tube.

Finally, a fourth exemplary embodiment of the present invention refers to a computer program for executing a method as described above with reference to said third exemplary embodiment when being implemented and running on an image acquisition control unit of a 3D tomosynthesis scanner apparatus.

BRIEF DESCRIPTION OF THE DRAWINGS

These and other advantageous aspects of the invention will be elucidated by way of example with respect to the embodiments described hereinafter and with respect to the accompanying drawings. Therein.

DETAILED DESCRIPTION OF THE EMBODIMENTS

In the following, the configuration of the proposed 3D tomosynthesis scanner apparatus and the particular steps of the image acquisition method according to the present invention will be explained in more detail with respect to special refinements and referring to the accompanying drawings.

Figure 1:
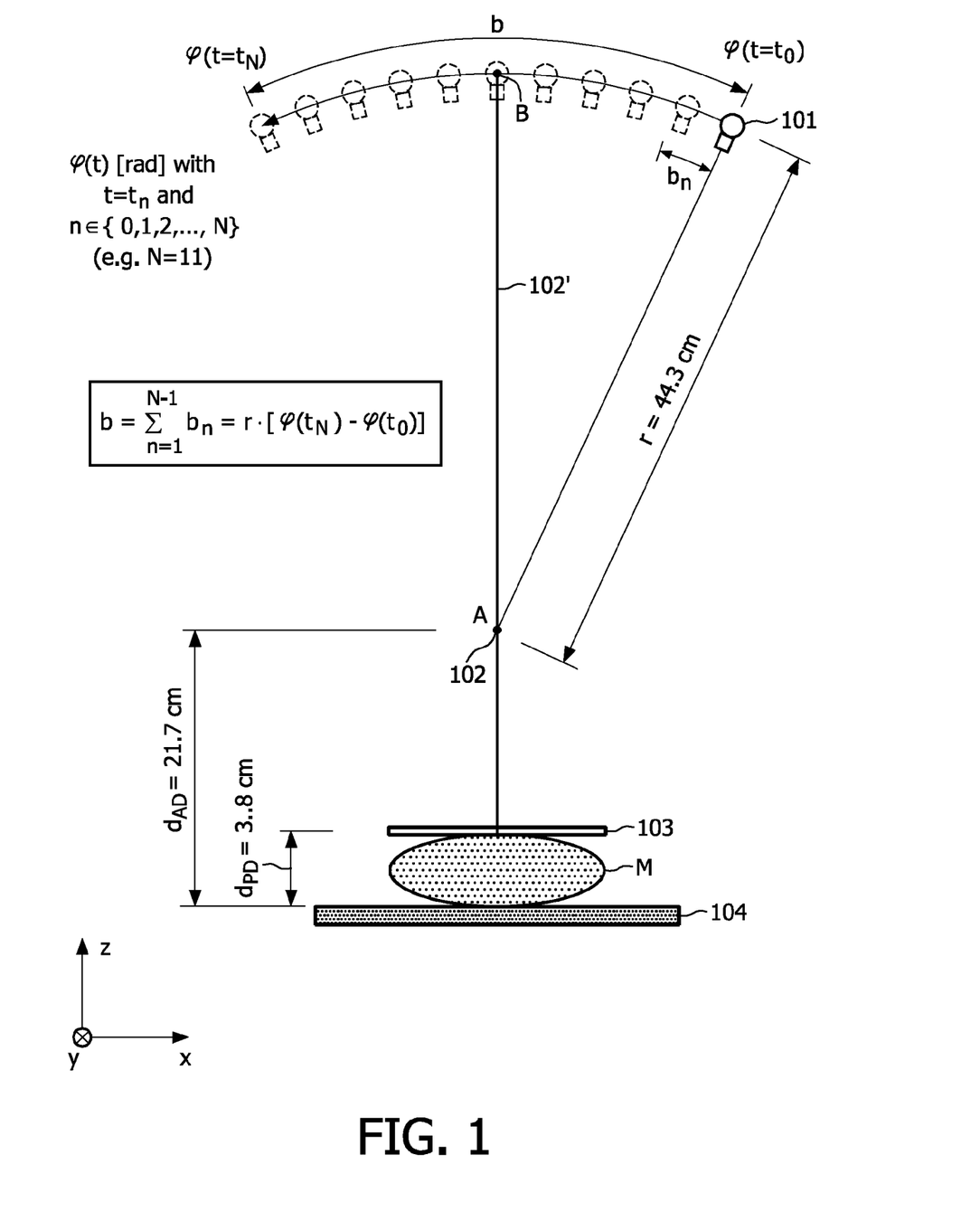
FIG. 1 shows a configuration of a conventional digital breast tomosynthesis scanner apparatus for use in CT mammography as known from the prior art in a schematic cross-sectional side view.

In FIG. 1, a typical configuration of a conventional digital breast tomosynthesis scanner apparatus for use in CT mammography as known from the prior art is shown in a schematic cross-sectional side view. The tomosynthesis scanner apparatus comprises a rotary X-ray tube 101 moving along an arc segment of a circular trajectory with radius r about a horizontal axis of rotation 102 running in y-direction of a stationary three-dimensional Cartesian coordinate system spanned by the orthogonal coordinate axes x, y and z and thus perpendicular to the drawing plane. Furthermore, a stationary X-ray detector 104 (such as e.g. a flat panel detector, a strip detector, a CT detector or any other kind of X-ray detector) diametrically oppositely arranged to the X-ray tube 101 with respect to a female breast tissue M to be examined, the latter being slightly compressed in vertical direction z by means of a horizontal compression paddle 103, is foreseen. The axis of rotation 102 in this example is chosen at a relatively large distance $d_{AM}=w_P+d_{AD}-d_{PD}$ from the compressed breast tissue M to be examined, wherein $w_P$ denotes the width of the compression paddle, $d_{AD}$ is the distance between the axis of rotation and the irradiated surface of the flat panel detector 104 and $d_{PD}$ stands for the distance between the compression paddle 103 and said flat panel detector 104. The actual length of distance $d_{AM}$ is, however, dependent on the respectively applied system design.

In the configuration depicted in FIG. 1, the center of rotation of X-ray tube 101 may be chosen on any position on a straight line [AB] going through point 102 with the starting point A of said line (here exemplarily depicted as being identical with point 102) lying on center line 102' in a position above the compressed breast tissue M to be examined and end point B of said line being the intersectional point of center line 102' with the arc segment of the circular trajectory along which X-ray tube 101 is moved. As an alternative to this configuration, said starting point A may also lie on any position in or below the compressed breast tissue M which is to be examined by means of X-ray radiography (not shown).

It can also be foreseen that the trajectory which describes the movement of X-ray tube 101 is given by a straight line through point B running in a direction which may preferably be perpendicular to line [AB]. The calculations required to calculate the resultant 2D projection images then need to be adapted accordingly, which is more difficult than for the case of moving X-ray tube 101 along an arc segment of a circular trajectory of radius r about a center of rotation on line [AB], such as e.g. given by the point denoted with reference number 102.

Instead of the two X-ray views per breast used for traditional mammography, the depicted digital breast tomosynthesis scanner apparatus e.g. allows to acquire up to about e.g. 55 2D projection images per imaging session, each taken from a different azimuthal position along the aforementioned circular arc segment, while exposing the patient to no more radiation than in traditional mammography. Based on these views, a computer (not shown) estimates the location of pathological structures (such as e.g. tumors or other cancerous tissue regions) within the examined breast tissue by using maximum likelihood expectation maximization, an algorithm co-developed by Brandeis University and the Massachusetts General Hospital (MGH).

Figure 2:
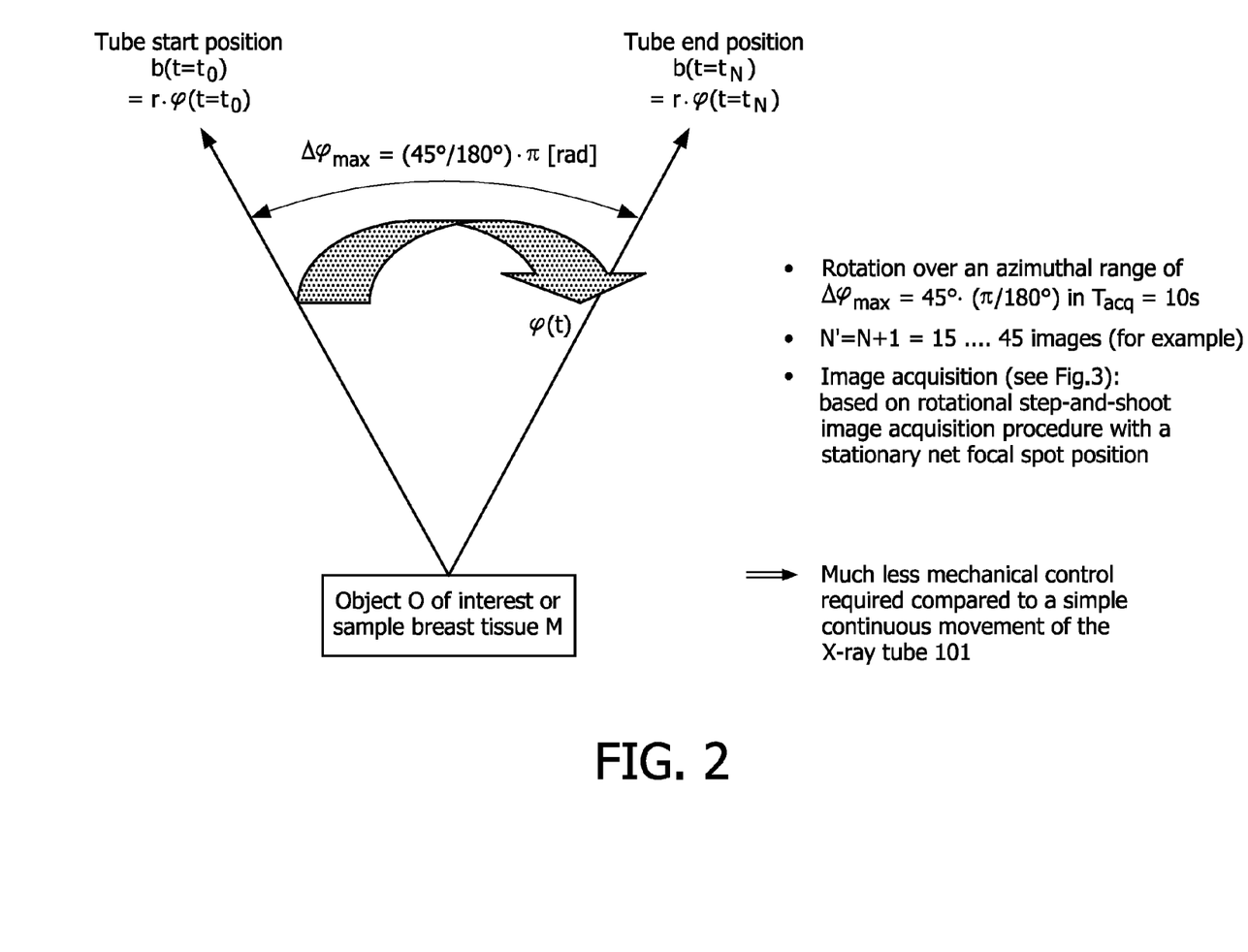
FIG. 2 is a schematic view of the proposed 3D tomosynthesis system according to the present invention and its system requirements.

As depicted in FIG. 2, which shows a schematic view of the proposed 3D tomosynthesis system according to the present invention and its system requirements, a rotary X-ray tube 101 is moved over an azimuthal range of e.g. $\Delta\phi_{max}=45°\cdot(\pi/180°)$ rad along an arc segment of a circular trajectory of radius r about a horizontal axis of rotation lying in the immediate proximity of an object of interest O or a sample breast tissue M to be examined, said arc segment starting at azimuthal position $b(t=t_0)=r\cdot\phi(t=t_0)$ and terminating at azimuthal position $b(t=t_N)=r\cdot\phi(t=t_N)$ with $t_n(n\in\{0, 1, 2, \ldots, N\})$ denoting N+1 discrete acquisition times. Thereby, $\phi(t=t_0)$ and $\phi(t=t_N)$ denote the corresponding azimuth angles given in radians at discrete times $t=t_0$ and $t=t_N$, respectively. During this rotational movement, between e.g. about 15 and 45 2D projection images obtained from distinct equidistant projection angles are taken within a total image acquisition time of e.g. $T_{acq}=10$ s. Thereby, $T_{acq}$ denotes the time difference between discrete times $t_0$ and $t_N$. The present invention thereby uses a method were the rotational movement of the X-ray tube can be executed in parallel with the image acquisition procedure by using an electron beam focal spot which is stationary when being seen from a stationary inertial system. The overlapping of integration time $T_{int}$ and time $T_{move}$ required to move the X-ray tube between the particular image positions thus leads to motion blur-free images in a much shorter total acquisition time $T_{acq}$. Furthermore, it can be stated that the proposed 3D tomosynthesis system and image acquisition method lead to a stationary net focal spot position while requiring much less mechanical control than conventional tomosynthesis systems based on a continuous rotational tube movement in conjunction with a simple stop-and-shoot method, whereupon 2D projection images can only be acquired during the integration times where said X-ray tube is stationary.

Figure 3:
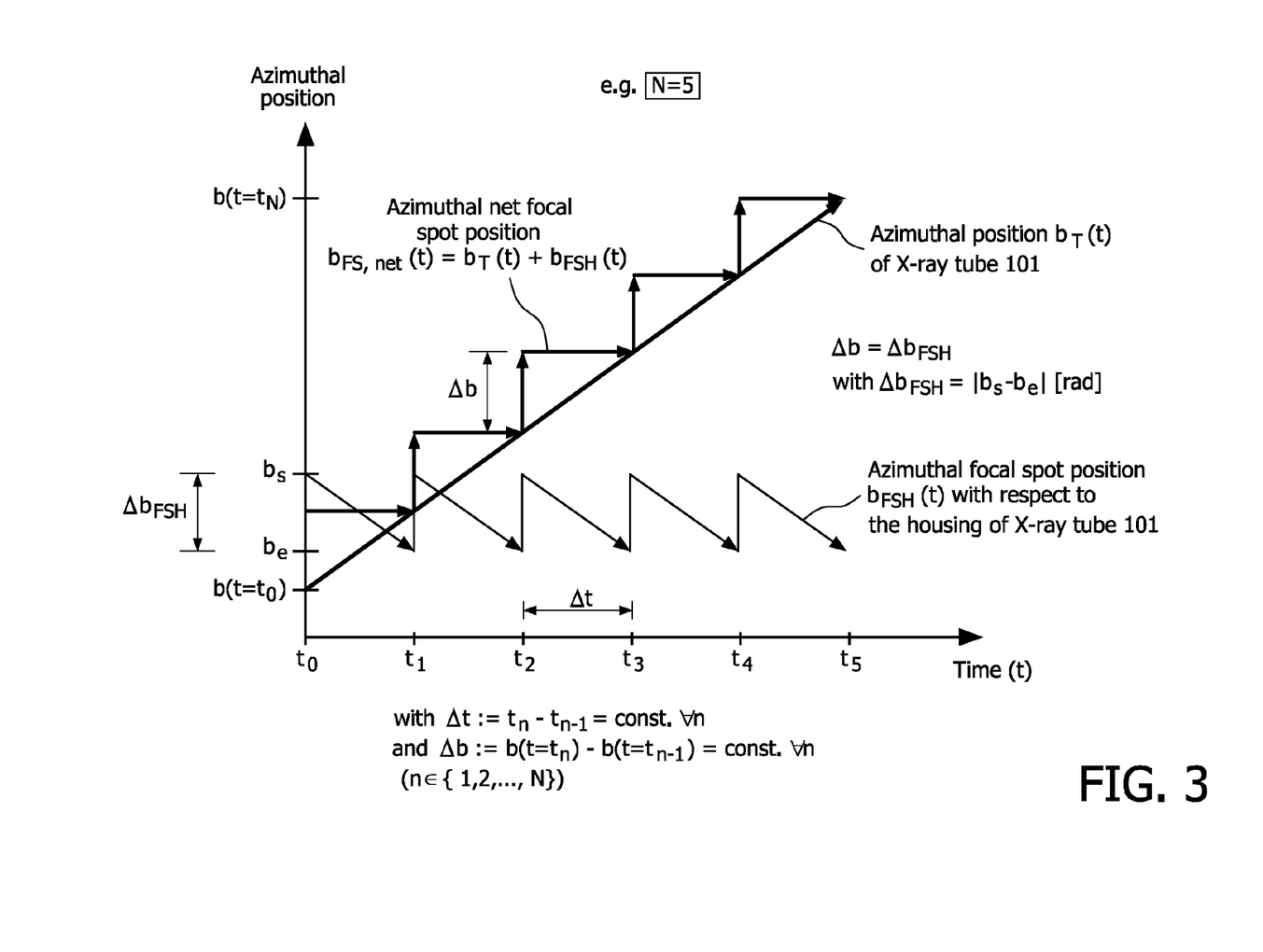
FIG. 3 shows a position-time characteristic for illustrating the proposed image acquisition method according to said third exemplary embodiment of the present invention which shows the net focal spot position in azimuthal direction along an arc segment of a circular trajectory on which the X-ray tube is moved about a rotational axis as a function of time, given as a superposition of the continuous tube movement when rotating about said rotational axis along this arc segment and focal spot movement in an opposite direction along the same arc segment within the tube housing of said X-ray tube.

Referring now the position-time characteristic as shown in the diagram of FIG. 3, the herewith proposed image acquisition method according to said third exemplary embodiment of the present invention shall be described in more detail. The figure shows the net focal spot position in azimuthal direction along an arc segment of length b of a circular trajectory with radius r on which rotary X-ray tube 101 is moved about said rotational axis as a function of time t, wherein the net position of the focal spot is given as a superposition of the continuous tube movement when rotating about the rotational axis along the aforementioned arc segment and azimuthal focal spot movement along this arc segment with respect to the tube housing of the X-ray tube, in said figure denoted as the graph of a discontinuous sawtooth function.

Due to the fact that the slope factor of sawtooth function $b_{FSH}(t) = r \cdot \phi_{FSH}(t)$ is the inverse slope factor of azimuthal tube position function $b_T(t) = r \cdot 100_T(t)$ with $\phi_{FSH}(t)$ and $\phi_T(t)$ given in radians denoting the corresponding azimuthal angle of the focal spot and the corresponding azimuthal angle of the X-ray tube on the same arc segment of the aforementioned circular trajectory as a function of time t, respectively, the resultant discontinuous function describing the net position of the electron beam focal spot on the X-radiation emitting surface of said rotary X-ray tube's anode has a slope factor which is equal to zero within each time frame $]t_n, t_{n+1}[$ for $n \in \{0, 1, 2, \ldots, N-1\}$.

As an alternative, the anode shape may be designed such that a relatively small change $\Delta b_{FSH}$ in the azimuthal position $b_{FSH}(t)$ of the electron beam focus within the rotary X-ray tube causes a relatively large change $\Delta b$ per time interval $\Delta t = t_n - t_{n-1}$ $\forall n$ in focal net position $b_{FS,net}(t) = b_T(t) + b_{FSH}(t)$ which compensates the slope factor of the aforementioned tube position function $b_T(t)$. The X-radiation emitting surface of said anode should thereby have a relatively steep contour.

To get an idea of the distance that the X-ray focus has to move in the tube, the following estimate is given: When the radial distance between the electron beam focal spot of rotary X-ray tube 101 and the axis of rotation 102 is e.g. r=60 cm and the aforementioned circular arc segment has an angular width of $\Delta\phi_{max} = 50° \cdot (\pi/180°)$ rad, total length b of this circular arc segment and thus the azimuthal path covered by said X-ray tube can be calculated as follows:

$$b = \sum_{n=1}^{N-1} b_n = r \cdot \Delta\varphi_{max} [\text{cm}] \text{ with} \quad (1a)$$

$$\Delta\varphi_{max} = \frac{\pi}{180°} \cdot |\varphi(t=t_N) - \varphi(t=t_0)| [\text{rad}], \quad (1b)$$

which yields b≈52 cm. Therein, $b_n$ denotes the arc distance between two adjacent image acquisition positions of the electron beam focal spot along this circular arc segment with $b_n$ having the same length for each value of n (for $n \in \{1, 2, \ldots, N-1\}$).

When the number of images that is acquired is e.g. N=30, the maximum distance the X-ray focus on the rotary X-ray tube's anode needs to travel is thus given by $$b_n = \frac{1}{N-1} \cdot b[\text{cm}] \forall n, \quad (1c)$$

thus yielding $b_n \approx 1.8$ cm. When more or less images need to be acquired, this number will change. Also, it is not absolutely necessary that a 100% duty cycle is obtained. The length of about 2 cm, however, will be a typical value.

Figure 4:
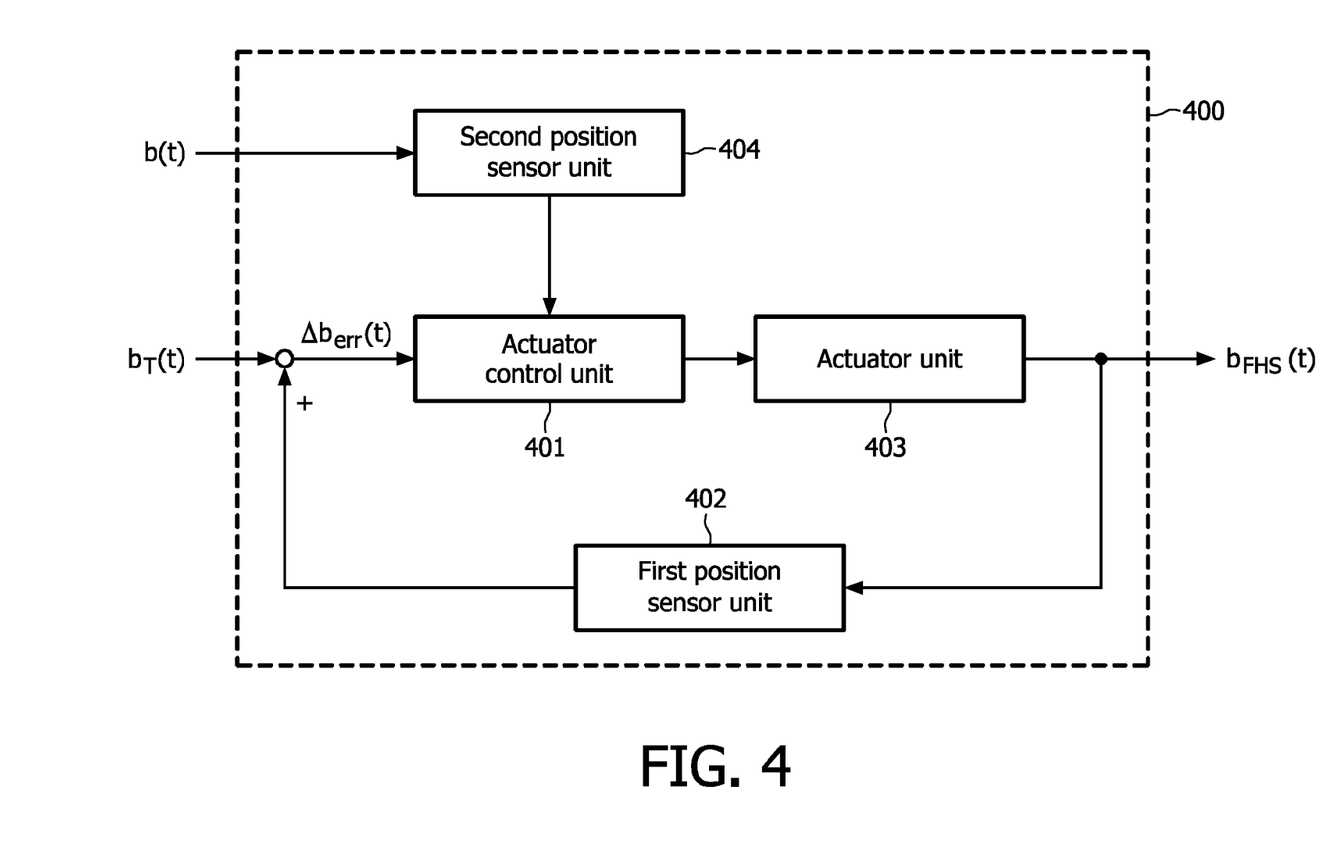
FIG. 4 shows a schematic block diagram of a closed-loop control circuit for controlling the movement of the electron beam focal spot on the rotary X-ray tube's anode in azimuthal direction with respect to the X-ray tube's housing.

In FIG. 4, a schematic block diagram of a closed-loop control circuit 400 for controlling the movement of the electron beam focal spot on the rotary X-ray tube's anode in azimuthal direction with respect to the X-ray tube's housing is shown. In a feed-back line, the closed-loop control circuit 400 comprises a first position sensor unit for continuously detecting momentary position $b_{FSH}(t)$ of the electron beam focal spot on the rotary X-ray tube's anode with respect to said X-ray tube's housing, the output signal of said first position detector being fed back to an input port of said actuator control unit. The feed-forward line comprises an actuator unit 403 for moving the electron beam focal spot on the rotary X-ray tube's anode from said start position $b_s$ to said end position $b_e$. An actuator control unit 401 which precedes said actuator unit is used for controlling the actuator unit 403 in a closed-loop control based on the momentary position $b_{FSH}(t)$ of the electron beam focal spot continuously as detected by said first position sensor unit 402 and based on the rotary X-ray tube's momentary position $b_T(t)$ on the arc segment of the of the circular trajectory as detected by a second position sensor unit 404.

Figure 5:
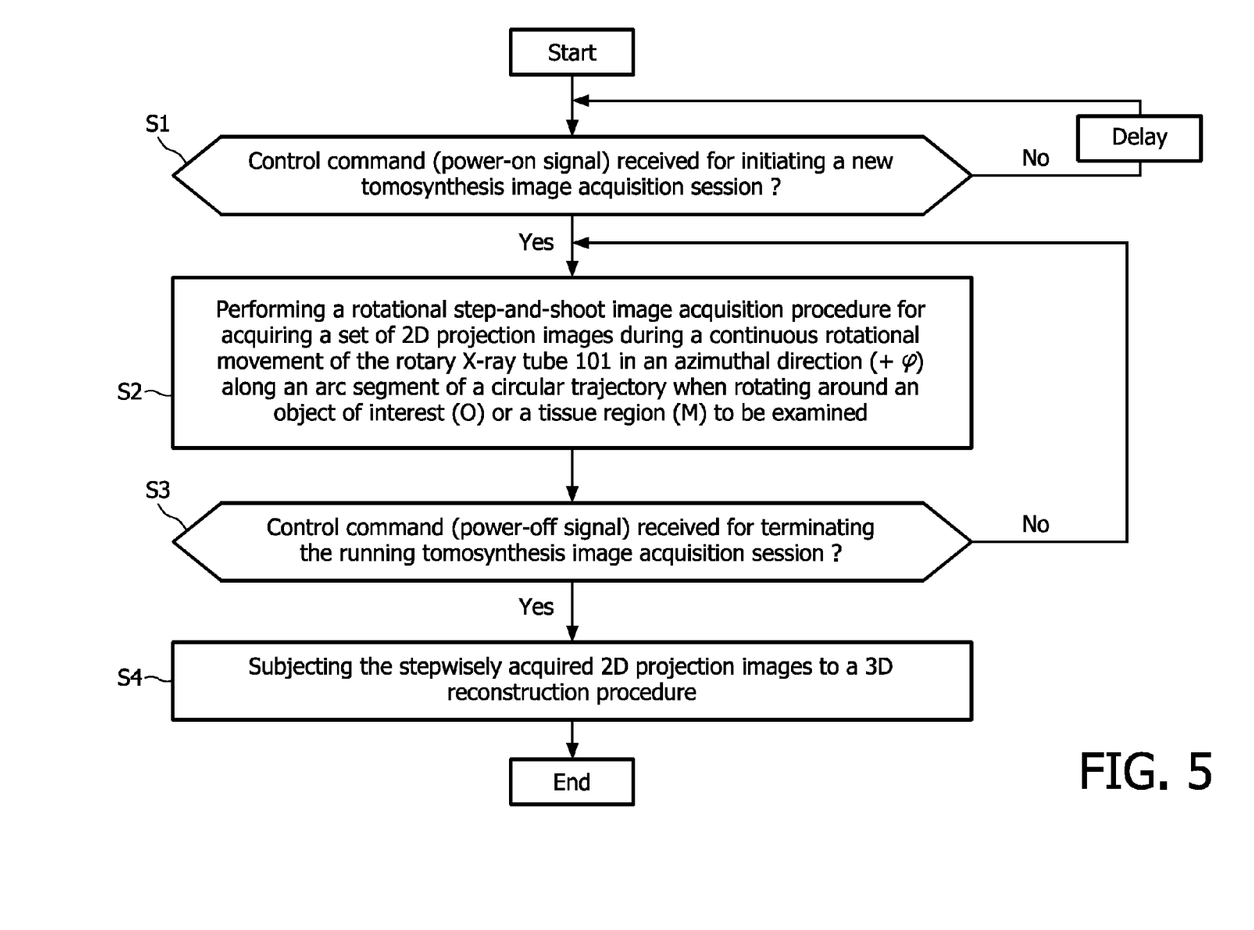
FIG. 5 shows a flowchart for illustrating the proposed image acquisition method according to said third exemplary embodiment of the present invention.

A flow chart for illustrating the proposed method for operating a 3D tomosynthesis scanner apparatus as described above with reference to said third exemplary embodiment is shown in FIG. 5. After having received (S1) a control command (or power-on signal) for initiating a new tomosynthesis image acquisition session, a rotational step-and-shoot image acquisition procedure for acquiring a set of 2D projection images during a continuous rotational movement of the rotary X-ray tube 101 in an azimuthal direction (+$\phi$) along an arc segment of a circular trajectory is performed when said X-ray tube 101 is rotating around an object of interest O or a tissue region M to be examined (S3). Otherwise, the procedure is continued in a loop with step S1 until such a control command or a power-on signal has been received. When receiving (S4) a control command (or power-off signal) for terminating the running tomosynthesis image acquisition session, the procedure is finished. Otherwise, it is continued with step S2 to be cyclically repeated in a loop until such a control command or power-off signal has been received.

APPLICATIONS OF THE PRESENT INVENTION

The present invention and the above exemplary embodiments can advantageously be applied in the scope of digital breast tomosynthesis systems as used in cone-beam volume CT mammography imaging so as to avoid motion artifacts and blurring effects. The number N of acquired images per image run may thereby vary from e.g. about 11 to 55.

An X-ray or CT scanner system as described above can e.g. be equipped with a flat panel detector, strip detector, CT detector or any other kind of X-ray detector based upon an amorphous silicon (α-Si) or a CMOS sensor array using a scintillator or a direct conversion material that is used to acquire image information in parallel with the readout of a previous image.

In this way, the rotary X-ray tube is permanently used for image acquisition without interruptions due to rotational movements of the X-ray tube (which means that $T_{int}$ is equal to $T_{acq}$), such that a duty cycle $$d = \frac{T_{int}}{T_{acq}} \cdot 100\% = \left(1 - \frac{T_{move}}{T_{acq}}\right) \cdot 100\% \quad (2)$$

of 100% is obtained. Consequently, total image acquisition time $T_{acq}$ which is required to obtain a complete image sequence consisting of N 2D projection images as needed for a subsequent 3D reconstruction algorithm and thus the time for the patient to remain completely still are minimized. When a detector is used that cannot use image integration and image readout in parallel, however, the duty cycle cannot be 100%, but still a significant reduction in the total required image acquisition time $T_{acq}$ can be obtained.

Although the concept of electron beam focal spot displacement as proposed in the scope of the present invention is described based on an application scenario with rotary X-ray tubes moving on an arc segment of a circular trajectory running about an axis of rotation, said concept can also be applied to configurations of an X-ray or CT scanner system comprising an array of sequentially switchable, spatially distributed X-ray tubes addressed by a programmable switching sequence which are non-rotationally attached to a stationary gantry. Thereby, it may be provided that the focal spot of an electron beam emitted by a cathode to which the respective anode targets of the particular X-ray tubes are exposed is displaced in order to avoid damaging of the applied anode material (e.g. by melting or cracking due to the heat which emerges at each X-ray tube's focal spot position). The stationary X-ray tubes may e.g. be of the carbon nanotube (CNT) type which implies the advantage of high spatial resolution and fast switching capability.

Besides the proposed system configurations described in this application, which refer to a digital breast tomosynthesis scanner apparatus and method, it may also be contemplated that the benefits of the invention described herein may be used for 3D tomosynthesis applications other than CT mammography. Additional, although the herein described method and apparatus are described as belonging to a medical setting, it is contemplated that the benefits of the invention may also accrue to non-medical imaging systems such as those systems typically employed in an industrial or transportation setting, such as, for example, but not limited to, a baggage scanning system for an airport or any other kind of transportation center.

While the present invention has been illustrated and described in detail in the drawings and in the foregoing description, such illustration and description are to be considered illustrative or exemplary and not restrictive, which means that the invention is not limited to the disclosed embodiments. Other variations to the disclosed embodiments can be understood and effected by those skilled in the art in practicing the claimed invention, from a study of the drawings, the disclosure and the appended claims. In the appended claims, the word "comprising" does not exclude other elements or steps, and the indefinite article "a" or "an" does not exclude a plurality. The mere fact that certain measures are recited in mutually different dependent claims does not indicate that a combination of these measures can not be used to advantage. A computer program may be stored/distributed on a suitable medium, such as e.g. an optical storage medium or a solid-state medium supplied together with or as part of other hardware, but may also be distributed in other forms, such as e.g. via the Internet or other wired or wireless telecommunication systems. Furthermore, any reference signs in the claims should not be construed as limiting the scope of the invention

The invention claimed is:

1. A 3D tomosynthesis scanner apparatus comprising a rotary X-ray tube and a stationary X-ray detector diametrically oppositely arranged to the X-ray tube, said 3D tomosynthesis scanner apparatus being adapted for performing a rotational step-and-shoot image acquisition procedure for acquiring a set of 2D projection images during a continuous rotational movement of an X-ray tube in an azimuthal direction (+φ) along an arc segment of a circular trajectory when rotating around an object of interest (O) or a tissue region (M) to be examined and subjecting these 2D projection images to a 3D reconstruction procedure, wherein, during the image acquisition time for each 2D projection image, the electron beam focal spot on the rotary X-ray tube's anode is moved in an opposite direction (−φ) along the same arc segment from a start position ($b_s$) to an end position ($b_e$) with respect to the rotary X-ray tube's housing such that the azimuthal path distance (Δb) covered by the X-ray tube due to the continuous rotational tube movement during this time is compensated.

2. The 3D tomosynthesis scanner apparatus according to claim 1,
comprising a mechanism for switching the electron beam focal spot back to its start position ($b_s$) with respect to said tube housing before starting a new image acquisition process for acquiring the image data of a next 2D projection image of said object of interest (O) or tissue region (M) to be examined.

3. The 3D tomosynthesis scanner apparatus according to claim 2,
said 3D tomosynthesis scanner apparatus being adapted, for performing a superposition of a compensation movement of said electron beam focal spot to the X-ray tube's continuous rotational movement, wherein said compensation movement is defined by a time-variant discontinuous sawtooth function ($b_{FSH}(t)$) describing said electron beam focal spot's momentary position over the time.

4. The 3D tomosynthesis scanner apparatus according to claim 3,
wherein said time-variant discontinuous sawtooth function is given by a stepwise linear function with an inverse slope factor as compared to the slope factor of a linear time-variant function ($b_T(t)$) describing the X-ray tube's momentary position over the time.

5. The 3D tomosynthesis scanner apparatus according to claim 4,
wherein the azimuthal path distance (Δb) to be compensated is a linear function of the difference in azimuth ($\Delta b_{FSH}$) covered by the electron beam focal spot when being moved from said start position ($b_s$) to said end position ($b_e$) with respect to the rotary X-ray tube's housing with the radial distance between the center of rotation and the focal spot position on the circular arc segment being a proportionality factor of this linear function.

6. The 3D tomosynthesis scanner apparatus according to claim 1,
comprising a first position sensor unit for detecting the momentary position ($b_{FSH}(t)$) of the electron beam focal spot on the rotary X-ray tube's anode with respect to said X-ray tube's housing.

7. The 3D tomosynthesis scanner apparatus according to claim 6,
comprising an actuator unit for moving the electron beam focal spot on the rotary X-ray tube's anode from said start position ($b_s$) to said end position ($b_e$) and an actuator control unit for controlling the actuator unit in a closed-loop control based on the momentary position ($b_{FSH}(t)$) of the electron beam focal spot continuously detected by said first position sensor unit and the rotary X-ray tube's momentary position ($b_T(t)$) on the arc segment of the of the circular trajectory, the latter momentary position being detected by a second position sensor unit.

8. The 3D tomosynthesis scanner apparatus according to claim 7,
wherein the actuator unit is equipped with a field generator device for generating an electric and/or magnetic field to deflect an electron beam impinging on the X-radiation emitting surface of said rotary X-ray tube's anode such that the resulting electron beam focal spot is moved along the circular trajectory from said start position ($b_s$) to said end position ($b_e$).

9. An image acquisition, processing, visualization and archiving system comprising a 3D tomosynthesis scanner apparatus according to claim 1.

10. A method for operating a 3D tomosynthesis scanner apparatus comprising a rotary
X-ray tube and a stationary X-ray detector diametrically oppositely arranged to the X-ray tube, said method comprising the steps of
performing a rotational step-and-shoot image acquisition procedure (S2) for acquiring a set of 2D projection images during a continuous rotational movement of the rotary X-ray tube in an azimuthal direction (+φ) along an arc segment of a circular trajectory when rotating around an object of interest (O) or a tissue region (M) to be examined and
subjecting these 2D projection images to a 3D reconstruction procedure (S3), wherein, during the image acquisition time for each 2D projection image, the electron beam focal spot on the X-ray tube's anode is moved in an opposite direction (−φ) along the same arc segment from a start position ($b_s$) to an end position ($b_e$) with respect to the rotary X-ray tube's housing such that the azimuthal path distance (Δb) covered by the rotary X-ray tube due to the continuous rotational tube movement during this time is compensated.

11. The method according to claim 10,
comprising the step of switching (S2d) the electron beam focal spot back to its start position ($b_s$) with respect to said tube housing before starting a new image acquisition process for acquiring the image data of a next 2D projection image of said object of interest (O) or tissue region (M) to be examined.

12. The method according to claim 11,
wherein the compensation of said azimuthal path distance (Δb) is achieved by a superposition of a compensation movement of said electron beam focal spot to the X-ray tube's continuous rotational movement, said compensation movement being defined by a time-variant discontinuous sawtooth function ($b_{FSH}(t)$) describing said focal spot's momentary position over the time.

13. The method according to claim 12,
wherein said time-variant discontinuous sawtooth function is given by a stepwise linear function with an inverse slope factor as compared to the slope factor of a linear time-variant function ($b_T(t)$) describing the X-ray tube's momentary position over the time.

14. The method according to claim 10, comprising the steps of
continuously detecting (S2a) the momentary position (b(t)) of the rotary X-ray tube during the continuous rotational movement around the object of interest (O) or tissue region (M) to be examined and
controlling (S2b) an actuator unit applied for moving (S2c) the focal spot on the rotary X-ray tube's anode along the arc segment of said circular trajectory from said start position ($b_s$) to said end position ($b_e$) with respect to the rotary X-ray tube's housing dependent on the momentary position ($b_T(t)$) of the rotary X-ray tube.

15. A computer program for executing a method according to claim 10 when being implemented and running on an image acquisition control unit of a 3D tomosynthesis scanner apparatus.

\* \* \* \* \*